US008112232B2

(12) United States Patent
Parkhurst et al.

(10) Patent No.: US 8,112,232 B2
(45) Date of Patent: Feb. 7, 2012

(54) SYSTEM AND METHOD FOR AUTOVERIFYING LABORATORY TEST RESULTS

(75) Inventors: Jason Parkhurst, Westfield, IN (US); John M. Ashley, Fishers, IN (US)

(73) Assignee: Beckman Coulter, Inc., Brea, CA (US)

( * ) Notice: Subject to any disclaimer, the term of this patent is extended or adjusted under 35 U.S.C. 154(b) by 777 days.

(21) Appl. No.: 11/701,677

(22) Filed: Feb. 2, 2007

(65) Prior Publication Data
US 2008/0186133 A1    Aug. 7, 2008

(51) Int. Cl.
*G01N 31/00* (2006.01)
(52) U.S. Cl. .............................. 702/22; 702/30; 702/31
(58) Field of Classification Search .................. 702/22, 702/30–32, 123; 705/2, 3; 717/109, 113; 715/967
See application file for complete search history.

(56) References Cited

U.S. PATENT DOCUMENTS

| | | | |
|---|---|---|---|
| 5,005,119 A | | 4/1991 | Rumbaugh et al. |
| 5,005,143 A | | 4/1991 | Altschuler et al. |
| 5,703,788 A | | 12/1997 | Shei et al. |
| 5,732,277 A | * | 3/1998 | Kodosky et al. ............. 717/125 |
| 5,786,816 A | | 7/1998 | Macrae et al. |
| 5,835,384 A | | 11/1998 | Lin |
| 5,850,221 A | * | 12/1998 | Macrae et al. ............... 715/853 |
| 6,063,132 A | | 5/2000 | DeCamp |
| 6,071,236 A | | 6/2000 | Iliff |
| 6,242,013 B1 | * | 6/2001 | Luhman et al. .................. 426/2 |
| 6,394,811 B2 | | 5/2002 | Finitzo et al. |
| 6,426,759 B1 | | 7/2002 | Ting et al. |
| 7,315,825 B2 | | 1/2008 | Rosenfeld et al. |
| 7,337,432 B2 | | 2/2008 | Dathathraya et al. |
| 2002/0128802 A1 | | 9/2002 | Rompala |
| 2003/0139903 A1 | | 7/2003 | Zweig et al. |
| 2003/0167265 A1 | | 9/2003 | Corynen |
| 2003/0191667 A1 | | 10/2003 | Fitzgerald et al. |
| 2004/0030578 A1 | * | 2/2004 | Cross et al. ....................... 705/2 |
| 2004/0033164 A1 | | 2/2004 | Naito |
| 2004/0209375 A1 | | 10/2004 | Diby et al. |
| 2005/0066263 A1 | | 3/2005 | Baugher |
| 2006/0136263 A1 | | 6/2006 | Fry et al. |

FOREIGN PATENT DOCUMENTS

| | | |
|---|---|---|
| EP | 0962872 A2 | 12/1999 |
| WO | WO 98/45679 A1 | 10/1998 |
| WO | WO 03/025585 A1 | 3/2003 |

OTHER PUBLICATIONS

"Rules Manual: Instrument Manager v8.05", Data Innovations, Inc., © 1994-2006, 126 pages.
PCT International Search Report and Written Opinion in Application PCT/US08/52566, mailed May 22, 2008, 5 pgs.
European Extended Search Report in Application 08714146.1, mailed Oct. 14, 2011, 7 pgs.

* cited by examiner

*Primary Examiner* — Manuel L Barbee
(74) *Attorney, Agent, or Firm* — Merchant & Gould P.C.

(57) ABSTRACT

A method of autoverifying clinical test results comprises displaying an autoverification process as a flowchart on a graphical user interface. The autoverification process is defined by a plurality of nodes and a plurality of edges connecting the nodes. The autoverification process is configured to evaluate a result and determine if the test result meets a predetermined criteria. The method further comprises receiving the test result and automatically performing the autoverification process on the test result. A system for creating and implementing the autoverification processes comprises a graphical user interface configured to display the autoverification process as a flowchart. The system includes an input configured to receive the clinical test result from a laboratory analyzer. The system also includes a processor configured to analyze the clinical test result according to the defined autoverification process.

24 Claims, 9 Drawing Sheets

SYSTEM AND METHOD FOR AUTOVERIFYING LABORATORY TEST RESULTS

CROSS-REFERENCE TO RELATED APPLICATIONS

This application is related to U.S. patent application Ser. No. 11/701,708, entitled "System and Method for Testing Autoverification Rules", which was also filed on Feb. 2, 2007.

FIELD

This disclosure relates to the field of laboratory testing, and particularly clinical diagnostic testing and pre-clinical testing and verification of related laboratory test results.

BACKGROUND

Clinical diagnostic tests are commonly used in the medical profession to assist in diagnosing various medical conditions of a patient. Clinical diagnostic tests refer to those tests where a laboratory conducts an analysis on a specimen/sample from a patient. The term "sample" or "specimen" as used herein is intended to refer to such substances taken from a body including, without limitation, blood, urine, tissue, saliva, or other body substances. Following analysis of the patient sample, the laboratory produces a test result. The test result is then used by the doctor or other medical professional to assist in the diagnosis of one or more medical conditions.

In addition to clinical diagnostic testing, specimens may also be analyzed in other environments, such as pre-clinical testing. Pre-clinical testing refers to situations where drugs or devices are tested in a laboratory setting using various samples. For example, a new drug may be administered to a patient, and the patient's blood may be monitored to determine the effects of the drug on the patient. The term "clinical test result" as used herein is intended to refer to test results produced from clinical diagnostic testing and/or pre-clinical testing.

In a hospital lab, a test order for a clinical diagnostic test is delivered from a doctor and received in the laboratory accompanied by a patient sample. The patient sample is analyzed on one or more laboratory instruments to obtain test results. Examples of laboratory analyzers used to analyze patient samples include flow cytometers, hematology analyzers, immunoassay analyzers, and electrophoresis analyzers. It will also be recognized that numerous other laboratory analyzers may be used to analyze patient samples. Furthermore, manual testing may also be performed on the sample by a laboratory technician to provide test results for the test order. Once a sample is analyzed in the laboratory, the fulfilled test order is sent back to the doctor in the form of a test result. In many environments, the test order is received electronically and the test results are reported electronically through a local area network which provides access to various information systems.

One task for the laboratory technician performing or overseeing clinical diagnostic tests is to validate the test results obtained from the laboratory analyzers or from manual testing. The need for validation is present because many problems can occur during the sample gathering and testing process. For example, a patient sample may be mislabeled, resulting in test results being reported in association with the wrong patient. As another example, the patient sample may have been improperly drawn or improperly handled, resulting in sample contamination and erroneous test results. Furthermore, a laboratory analyzer may be either malfunctioning or drifting out of calibration, again causing the analyzer to report erroneous results.

Abnormal test results do not necessarily indicate erroneous results, but may instead indicate a serious medical problem. In such cases, it may be important for the lab technician to report the test results immediately to the doctor or other medical professional in addition to the normal reporting procedure of making the test results electronically available through a database. In these situations, the test results indicating a critical condition may call for the lab technician to make an immediate and confirmed report to the doctor, such as by telephone or in person.

Suspicious or abnormal test results may have a significant affect on the technician's workflow. A test with a questionable or abnormal result may need to be rerun by the technician to confirm that validity of the abnormal test result. In certain rerun situations where the sample concentration appears to be too high for the laboratory instrument, a dilution of the sample may be necessary before the rerun test is performed. Furthermore, certain tests or test results may cause subsequent tests to be ordered or cancelled. For example, an abnormally low or high test result may call for a rerun of the previously executed test to confirm that the previous test result is correct. This process of running tests, evaluating test results, rerunning tests, recalculating test results, and reporting test results to medical professionals makes the task of managing the laboratory and its workflow a complex task.

Evaluating test results can, in many cases, be done automatically by a computer. This process of using a computer to automatically evaluate laboratory test results is called autoverification (or autovalidation). Using autoverification, a test result from a laboratory analyzer is sent to a computer for evaluation. If the computer determines that the test result meets predetermined criteria established by the laboratory, the test result is approved and automatically released to the doctor. Test results that fail autoverification are held for manual review by the lab technician. Upon manual review, the lab technician may decide upon certain actions, such as releasing the test result, calling for a new test, calling for a new patient sample, calling for service on the laboratory analyzer, requesting confirmation of input data, or various other actions.

In many clinical diagnostic laboratories, laboratory tasks may be automated by the system. For example, many tests can be ordered or cancelled automatically. Dilutions can be done by some analyzers, and robotics or other equipment can allow samples to be automatically rerun. Thus, while the laboratory technician retains many important jobs in the laboratory, automation has reduced the number of jobs required of the technician, and has helped to make processes in the clinical diagnostic laboratory more efficient.

The release of actual test results from the clinical diagnostic laboratory is typically staged. In particular, "raw" test results from the laboratory analyzer are typically held in the laboratory's own database and computer system, often referred to as the laboratory information system ("LIS"). These raw test results are typically not released for viewing outside of the laboratory until they are approved by the lab. As mentioned above, raw test results may be approved automatically by an autoverification process or manually following review by a lab technician. Once test results are approved, the test results are released to a hospital or other medical facility's database and computer system, often referred to as the hospital information system ("HIS"). Doctors and other care providers have access to the approved test results in the HIS, but only the laboratory staff has access to unapproved results in the LIS.

Existing laboratory information systems attempt to provide autoverification capabilities by having the user write a series of "if/then" rules that are evaluated by the computer when test orders are received, test results are obtained, and/or results are uploaded to the HIS. These if/then rules essentially amount to a text-based programming language where the user is expected to write the complete autoverification process with the provided language. However, laboratory technicians are not typically trained in computer programming skills and find it difficult to write the autoverification rules based on the common text-based language. In addition, even for accomplished programmers, the provided language is typically awkward, and it is easy for the programmer to neglect certain aspects of the desired autoverification rule which is displayed as a confusing list of textual statements. Furthermore, once an autoverification process is defined using such systems, it is difficult for a laboratory technician to pull the defined autoverification process at a later time and easily determine the workflow within the process, since the series of textual "if/then" statements are difficult to follow. Accordingly, it would be advantageous to provide an autoverification system where autoverification processes created using the system are easily defined by the user and quickly and easily understood when presented to the user at a later time.

In addition to the awkward language used to define autoverification rules, existing systems also do not assist the technician in handling additional workflow associated with the autoverification process. In particular, execution of an autoverification rule may call for a test rerun or an associated test before the test results are verified. When such additional testing is ordered with existing systems, the extent of support is typically a notice that additional testing is required along with instructions on what the technician should do next. The technician must then act on the notice and order the additional testing before the autoverification process can be completed. Accordingly, it would be advantageous to provide an autoverification system that provides a means for either partially-automating or fully-automating workflow that needs to be done by the technician.

SUMMARY

A method of autoverifying clinical test results is disclosed herein. According to at least one embodiment, the method comprises displaying an autoverification process as a flowchart on a graphical user interface. The autoverification process is configured to evaluate a result and determine if the test result meets a predetermined criteria. The method further comprises receiving the test result and automatically performing the autoverification process on the test result.

According to another embodiment of the method, a plurality of nodes are selected from a menu of nodes when building the autoverification process. The selected plurality of nodes are configured and connected together. The configured and connected nodes define the autoverification process. Once the autoverification process is defined, clinical test results may be autoverified according to the autoverification process.

A system for performing the autoverification process is also disclosed herein. The system comprises a graphical user interface configured to display the flowchart defining the autoverification process. The system includes an input configured to receive the clinical test result from a laboratory analyzer. The system also includes a processor configured to analyze the clinical test result according to the defined autoverification process.

The above described features and advantages, as well as others, will become more readily apparent to those of ordinary skill in the art by reference to the following detailed description and accompanying drawings.

DESCRIPTION

Figure 1:
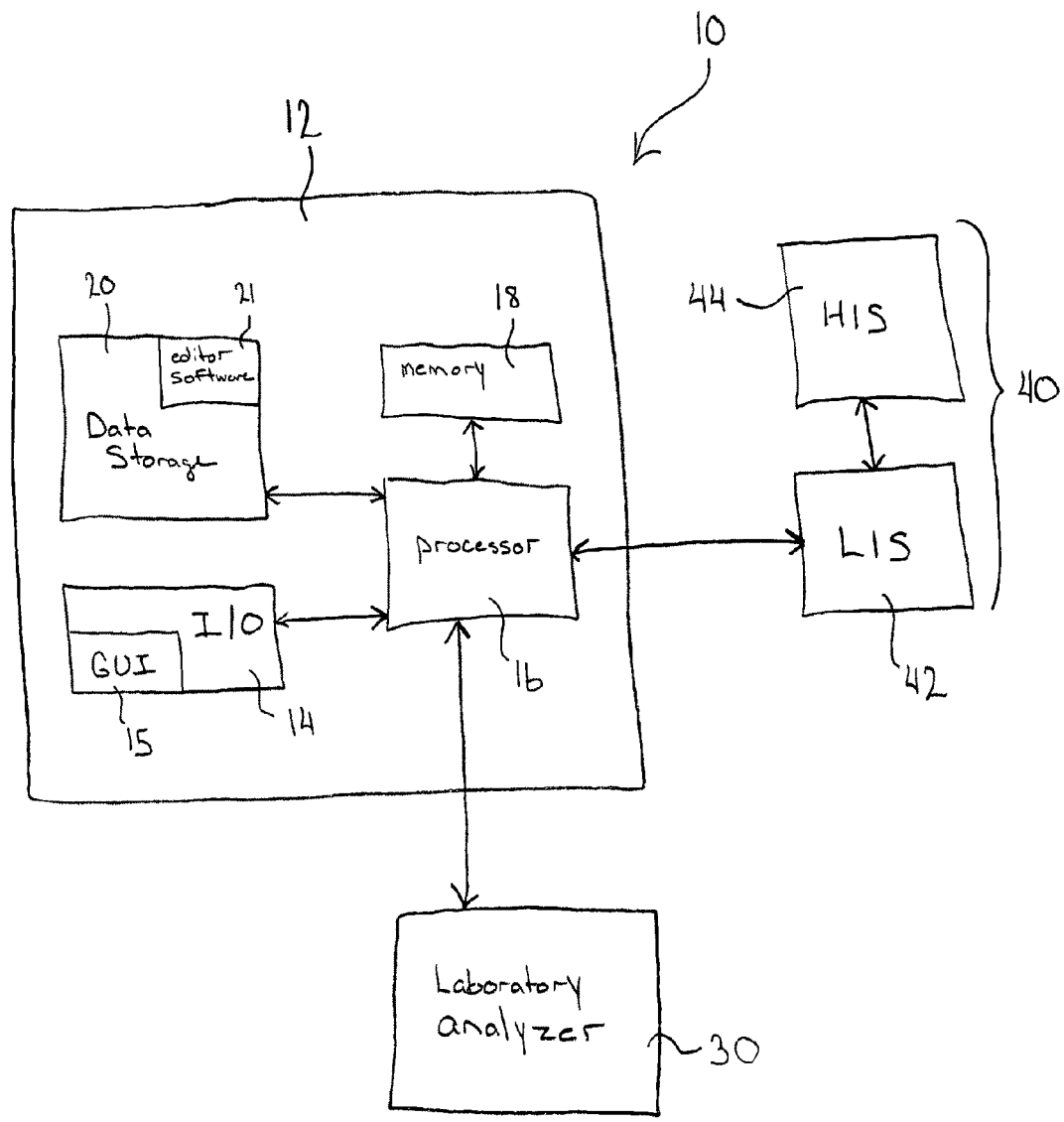
FIG. 1 shows a block diagram of a system for autoverifying laboratory test results, including a graphical user interface.

With reference to FIG. 1, an exemplary system for autoverifying laboratory test results is shown. The system 10 is provided as a computer 12 including input/output devices 14, a processor 16, a memory 18, and data storage 20. The computer 12 is connected to a laboratory analyzer 30. The computer 12 and the laboratory analyzer 30 are also connected to a network 40. The network 40 includes a laboratory information system (LIS) 42 and a hospital information system (HIS) 44 in communication with the LIS. The LIS and HIS include databases configured to retain test results available for viewing through either the HIS or the LIS, as permission to view the test results is granted by the system.

When a test order is received in the clinical laboratory, it is accompanied by a patient sample. The laboratory analyzer 30 is configured to perform a test on the patient sample and provide a test result that may be used for clinical diagnostic purposes. Exemplary laboratory analyzers include hematology analyzers, flow cytometers, immunoassay analyzers, protein analyzers, and electrophoresis analyzers. However, it will be recognized that any of numerous other laboratory analyzers capable of analyzing a sample and providing a test result may also be utilized. Manual testing may also be performed on the sample, such as viewing tissue under a microscope, and the results of such analysis may be manually entered into the system. In addition, while only a single laboratory analyzer 30 is shown in FIG. 1, it will be recognized that a plurality of laboratory analyzers may be connected to the computer and configured to provide test results to the computer. While the laboratory analyzer of FIG. 1 is shown connected directly to the computer 12, the laboratory analyzer 30 may instead be connected to a network along with other analyzers. For example, the laboratory analyzer 30 may be connected to the LIS 42, and test results from the laboratory analyzer may be reported to the computer through the LIS 42.

The computer 12 includes various input/output devices 14 configured to communicate with the lab technician or other operator/user. For example, one output device is a graphical user interface 15 which comprises a screen capable of displaying graphical images to the operator. Exemplary graphical user interfaces 15 comprise CRT screens and LED screens. The computer 12 further comprises various input devices 14, such as a mouse, touchscreen, keyboard, etc., which allow the operator to provide inputs to the computer 12.

The processor 16 is in communication with the input/output devices 14 and generally controls the flow of data within the computer, processes various instructions, and performs calculations. The processor 16 is further connected to the memory 18, and the data storage device 20, such as a hard drive. Software programs are stored on the data storage device 20 and memory 18, and the instructions provided by the software programs are executed by the processor 16.

One software program stored on the computer 12 is an autoverification rule editor 21. The editor software 21 works in association with the processor 16 and the graphical user interface 14 and allows the user to easily create autoverification processes (also referred to herein as "autoverification rules"). In particular, the editor 21 uses a flowchart-based language which allows the user to create autoverification rules as flowcharts. As discussed previously, autoverification rules are configured to evaluate test results provided by the laboratory analyzer 30 and determine if the laboratory test results meet certain predetermined criteria established by the laboratory.

Figure 2:
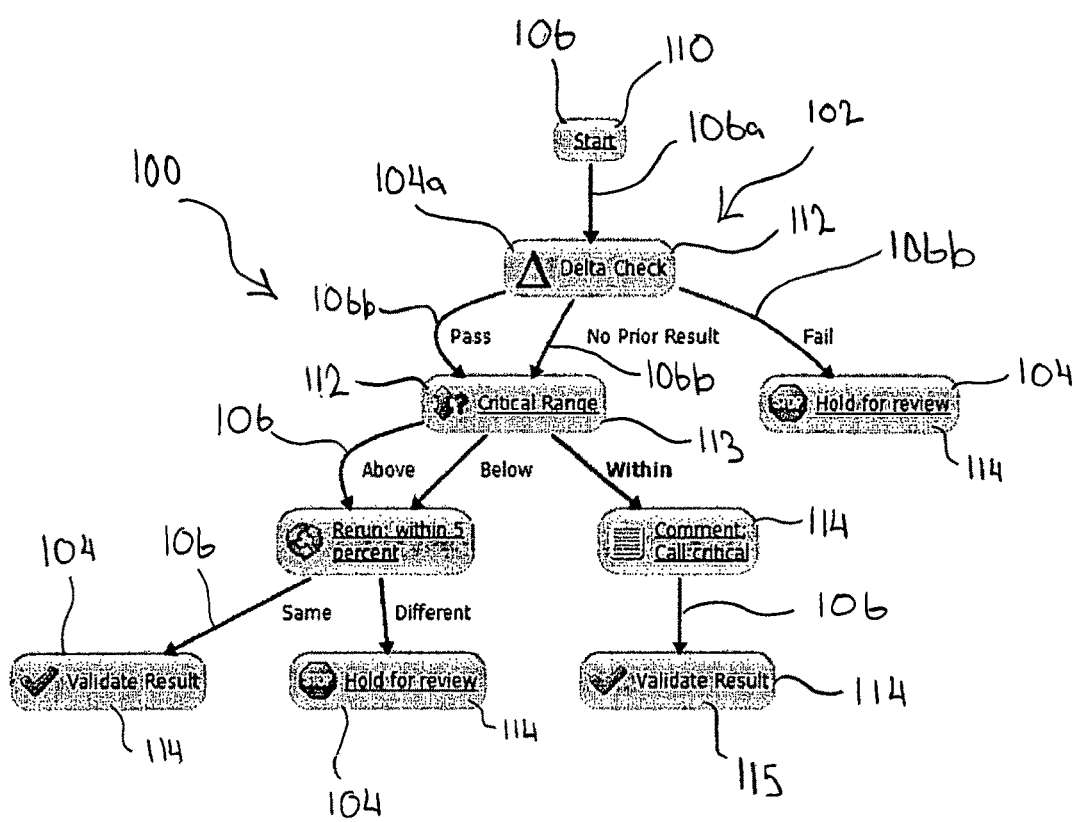
FIG. 2 shows an exemplary autoverification process in the form of a flowchart created using the system of FIG. 1.

With reference now to FIG. 2, an exemplary autoverification rule 100 created with the editor is shown as seen by the user on the graphical user interface 14. The term "autoverification rule" or "autoverification process" as used herein references the instructions and processes used to evaluate laboratory test results as well as the workflow involved with the evaluation process. Accordingly, an autoverification rule may comprise instructions to perform testing or take some other action on a sample in addition to evaluating test results.

In FIG. 2, the autoverification rule 100 is displayed in the form of a flowchart 102. The flowchart 102 provides a schematic representation of the autoverification rule and comprises a plurality of nodes 104 and a plurality of edges 106 connecting the nodes. Some action, instruction or analysis occurs at each node 104. The edges 106 define a workflow between the plurality of nodes 104, showing the direction of progress from one node to another node within the flowchart 102. Accordingly, a given node (e.g., node 104*a*) may be connected to input edges 106*a* indicating progress into the node and/or output edges 106*b* indicating progress out of the node. If more than one output edge 106*b* extends from a node 104, the output edges 106*b* extending from the node 104 will also indicate a contingency required before following the edge (e.g., "pass", "fail", "above", "below", etc.).

The nodes 104 are shown as box-like structures in the embodiment of FIG. 2, but it will be recognized that the nodes 104 may also be displayed in other forms. Similarly, the edges 106 are shown as arrow-like symbols in FIG. 2, but it will be recognized that the edges 106 may also be displayed in other forms.

The nodes 104 available for use in building a flowchart using the editor comprise start nodes 110, decision nodes 112, and action nodes 114. Each autoverification rule includes one start node 110. Execution of the autoverification rule begins with the start node 110. An exemplary start node 110 is shown in FIG. 2 at the top of the flowchart 100.

Decision nodes 112 are those nodes where a decision is made to proceed to one of a plurality of other nodes based on an input. For example, a decision node may check information provided about a patient, a specimen from the patient, one or more test results from a laboratory analyzer, or other information. After analyzing the input, the node determines a process flow based on the input information. Accordingly, each decision node includes two or more output edges 106*b*.

An exemplary decision node 112 shown in FIG. 2 is the range node 113. As described in further detail below, a range node 113 is configured to determine whether an input is above a predetermined range, below a predetermined range, or within a predetermined range. Accordingly, the range node 113 includes three output edges, each indicating a path to a different node depending upon whether the input is above the given range, below the given range, or within the given range.

Action nodes 114 are those nodes where some action, notice, or other side-effect occurs in the system as a result of execution of the node. For example, an action node may comprise validating a test result, releasing a test result to a higher level information system, holding a test result for review by a technician, adding a comment to a test result, ordering a dilution or test rerun, canceling a test, or calculating test results. Accordingly, action nodes are available to define the workflow associated with a particular autoverification rule, such as the ordering of tests, dilutions, or reruns. Action nodes may have one or more input nodes, but have only one or zero output nodes, as no decisions are made in an action node.

An exemplary action node 114 shown in FIG. 2 is the validate result node 115. When execution of the autoverification rule 100 reaches the validate result node 115, the system has evaluated the test result and confirmed that it meets certain predetermined criteria. At this point, the test result may be released to a higher level information system, where before validation the test result was only available to laboratory personnel using the laboratory information system. Following validation and release of the test result to the higher level information system, the test result may be viewed by medical personnel, such as doctors, on the hospital information system.

Figure 3:
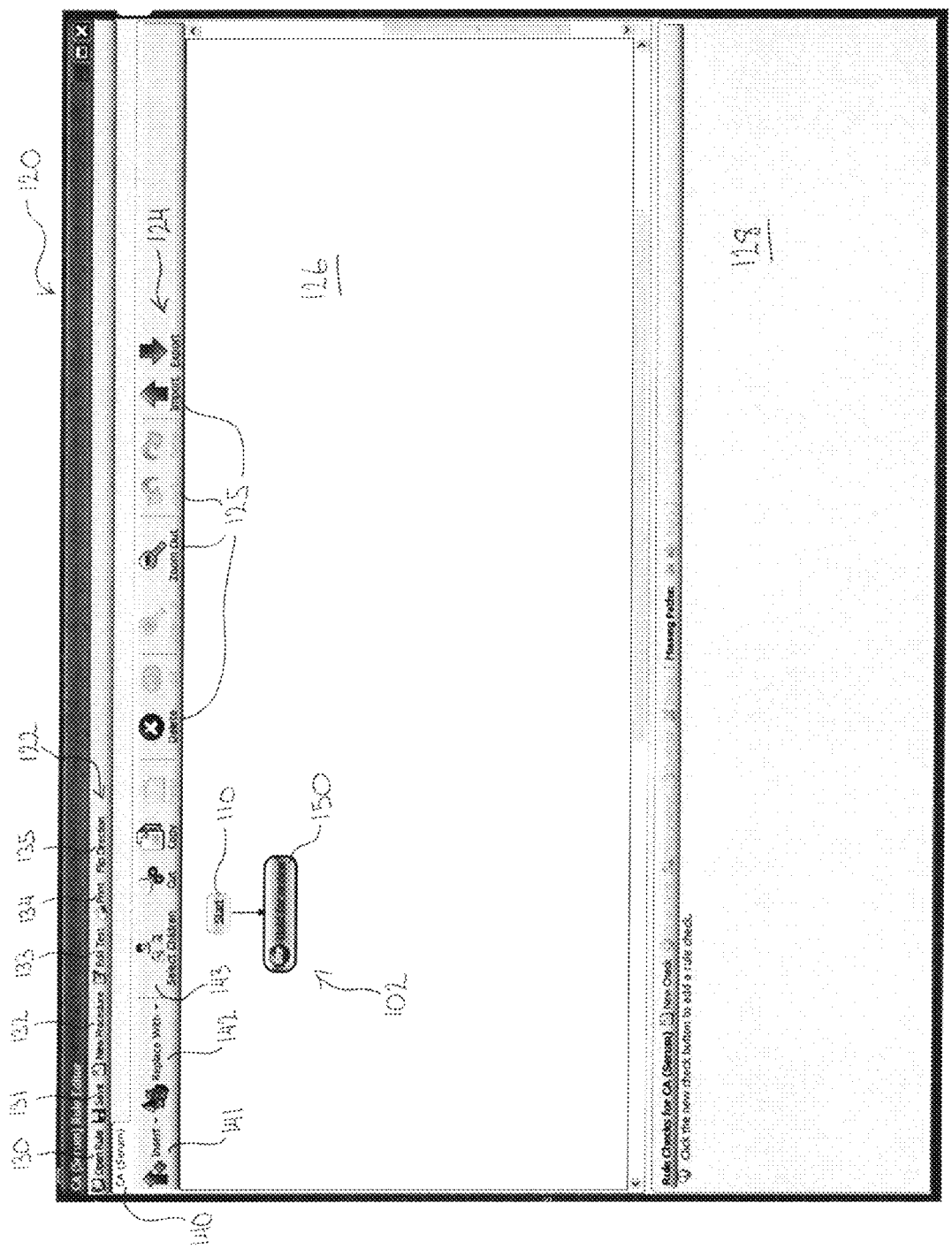
FIG. 3 shows an exemplary flowchart for an autoverification process displayed on a screen of the graphical user interface of FIG. 1.

Use of the editor to create autoverification rules is now described with reference to FIGS. 3-8. FIG. 3 shows an embodiment of the editor 120 as may be seen on the screen of the graphical user interface. The editor 120 comprises a top menu 122, a toolbar 124, a rule builder window 126, and a rule check window 128.

The top menu 122 of the editor provides the user with access to various sub-menus 130. By selecting one of the sub-menus 130-135, the user is provided with a list options related to the sub-menu. For example, by selecting the "open rule" submenu 130, the user one of several options, such as opening a new rule or opening an existing rule. Other sub-menus listed on the top menu include the "save" 131, "new procedure" 132, "edit test" 133, "print" 134, and "flip direction" 135 sub-menus. The tab 140 just below the top menu 122 indicates the autoverification rule shown in the rule builder window 126. As shown by the tab 140, the autoverification rule currently displayed in the rule builder window 126 of FIGS. 3-8 is for the serum calcium test.

The toolbar 124 is provided below the top menu 122. The toolbar 124 lists a plurality of commonly used options and displays the options as buttons 125. This allows the user to simply select the button 125 on the toolbar representing the desired option rather than going to the top menu 122 and its sub-menus to find the option. The buttons 125 provided on the toolbar may be changed by the user to provide buttons representing the most commonly used options of the user. In FIG. 3, the toolbar is shown with several buttons, including the "insert" option 141, "replace with" option 142, and "select children" option 143. Each of these options is described in further detail below with respect to the rule builder window 126 and FIGS. 3-8. FIGS. 3-8 also show other options on the toolbar 124, and it will be recognized that these or different options may be provided on the toolbar in various embodiments as determined by the user.

As mentioned above, the editor's rule builder window 126 displays a selected autoverification rule 100 in flowchart form 102. The autoverification rule 100 displayed in the rule builder window 126 may be saved, edited, or executed such that a test order is subjected to the rule check.

With continued reference to FIG. 3, assembly of an autoverification rule begins when the "new procedure" option 132 is selected from the top menu 122. When this option 132 is selected, a start node is automatically inserted into the rule builder window 126. Additional nodes may be obtained by selecting the "insert" option 141 on the toolbar 124. Upon selecting the "insert" option 141, the user is presented with a drop down menu of nodes that may be used in the rule. The drop down menu associate with the "insert" option 141 includes a list of various decision nodes, various action nodes, and a start node. In order to insert a node 110 in the rule builder window 126, the user simply clicks on the node selection from the drop down menu, and the selected node appears in the rule builder window. To connect a selected node 110 to another node existing in the rule builder window 126, the user clicks on the selected node 110 and drags it to make the desired connection to another node within the window.

As mentioned in the previous paragraph, the drop down menu associated with the "insert" option 141 provides a list of various action nodes and various decision nodes in addition to the start node. Exemplary action nodes include the following nodes:

Validate—This node validates a test result, (i.e., approves its release);
Hold—This node holds a test result for manual review by the lab tech;
Order Test—This node orders a test on a sample;
Cancel Test—This node cancels a test on a sample if a test exists;
Rerun—This node reruns the previous test; as an option, the new result from the rerun test can be compared against the previous test result and a decision made as to whether or not the new test result is sufficiently close to the previous test result;
Dilute—This node orders a dilution of the sample and a rerun of the previous test on the diluted sample;
Manual Workflow—This node describes a manual, offline workflow to be completed by the lab technician;
Add Comment—This node adds a comment to the result for the lab tech's attention;
Cap Result—This node caps a result to a specified numeric interval;
Set Value—This node sets the test result to a value built using an expression editor that allows arithmetic expressions built from constants as well as properties of the patient, sample, and test result; the expression must evaluate to an acceptable test result.
Exemplary decision nodes include the following nodes:
Critical Result Check—This node determines if a test result is a critical value;
Range Check—This node determines if a test result is inside, below, or above a validation range;
Delta Check—This node compares the test result to the last approved test result from the patient for the same test;
Check for Flags—This node determines if one or more flags were returned from the analyzer for the test result;
Check Condition—This node determines if a condition built using an expression editor that allows arithmetic and boolean expressions built from constants as well as properties of the patient, sample, and test result; the condition evaluates to true or false;
Check if Test is Ordered—This node determines whether or not a test is already ordered for the sample.

While the above lists describe various exemplary nodes, it will be recognized that these lists are not exhaustive, and numerous other nodes may be provided for use with the autoverification system and displayed in the menus.

Figure 4:
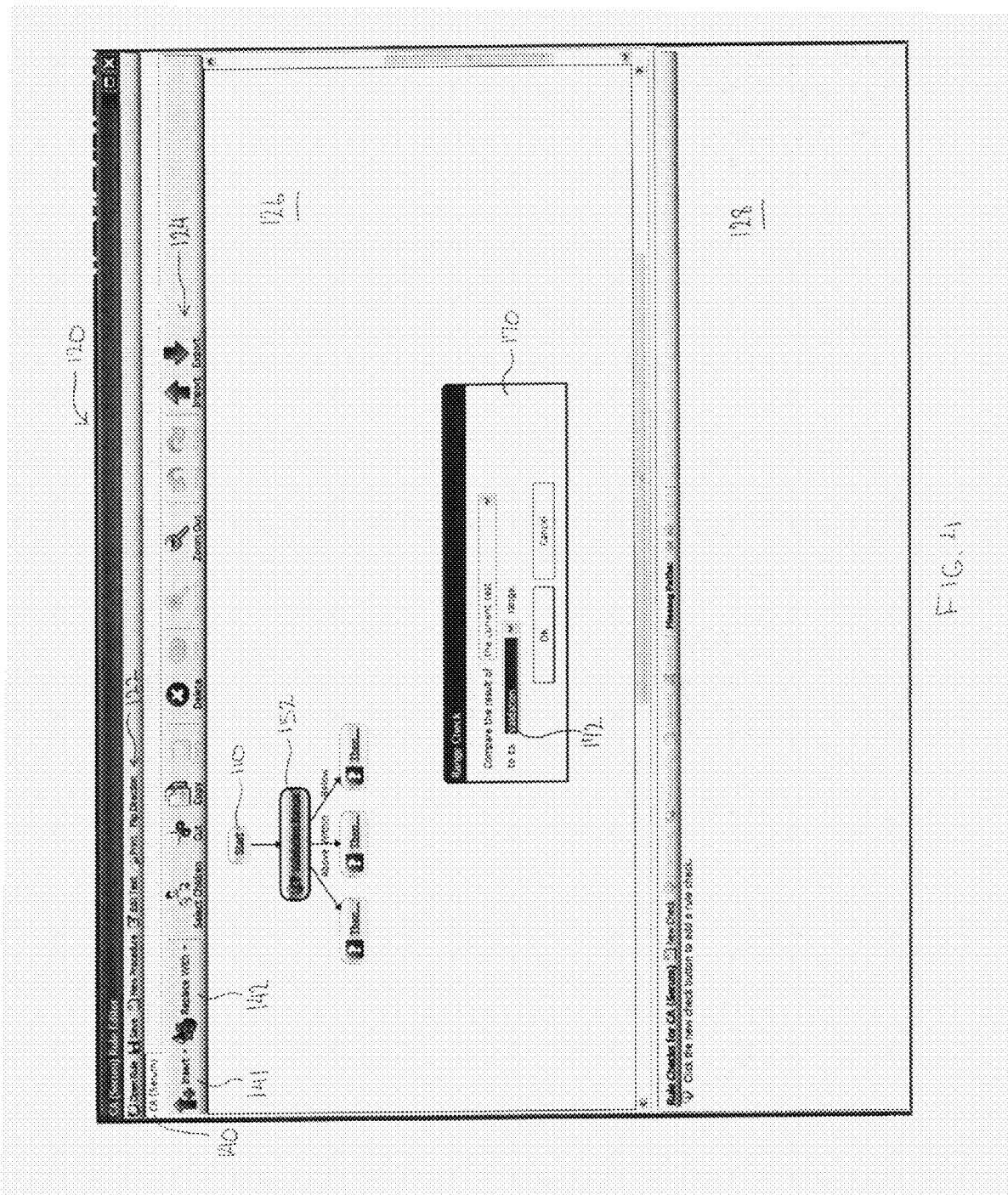
FIG. 4 shows the exemplary flowchart of FIG. 3 with an exemplary configuration box displayed on the screen along with the flowchart.
Figure 5:
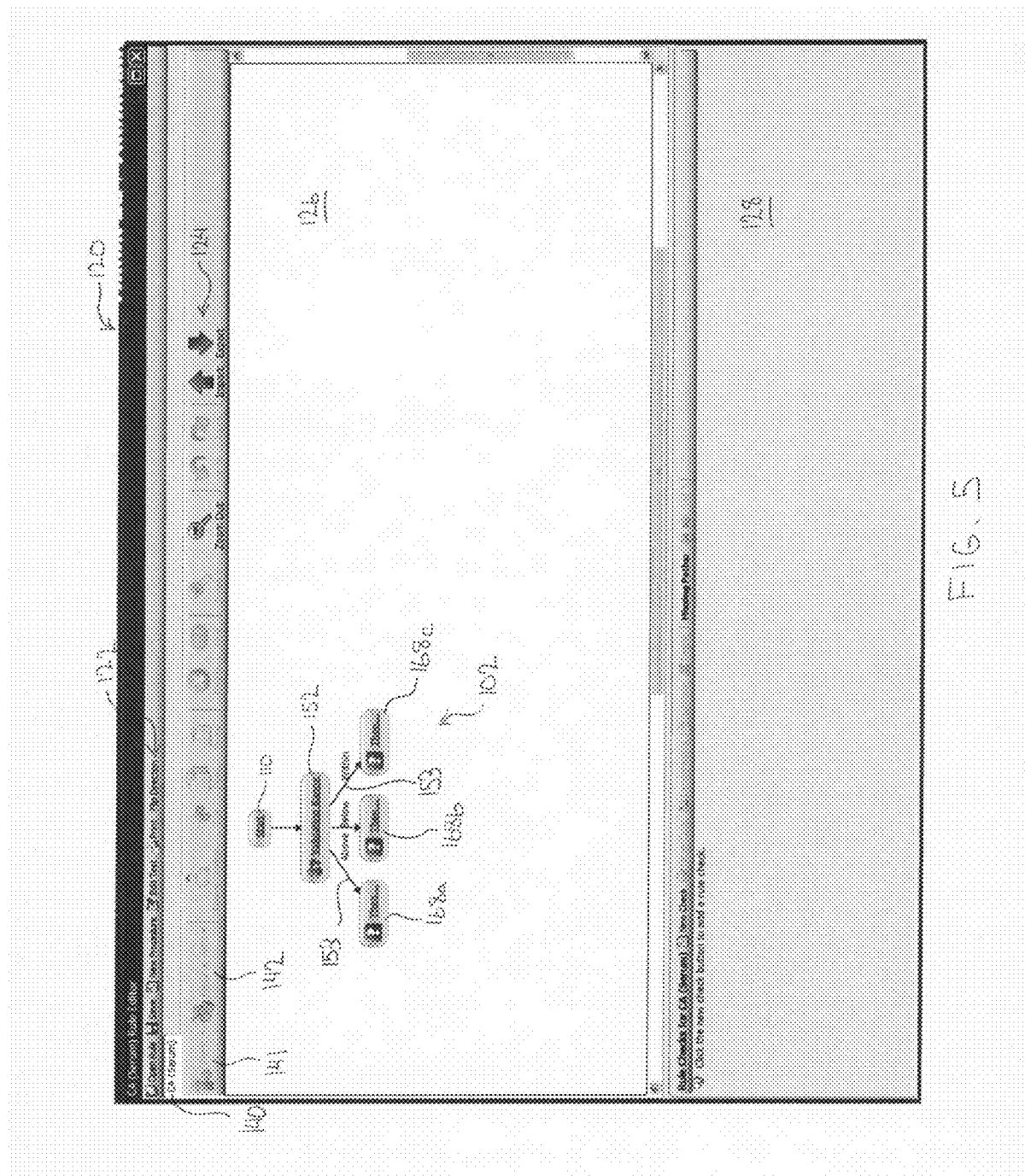
FIG. 5 shows the exemplary flowchart of FIG. 4 with a decision node having a plurality of output edges.

Returning to the example of FIG. 3, the user has inserted a hold node 150 in the rule builder window 126 and connected it to the start node 110. In addition to inserting nodes, the user may easily replace a node inserted into the rule builder window with a different node. In order to do this, the user first clicks on the node to be replaced in the rule builder window. When a node is selected by clicking on the node, the node is highlight in the rule builder window. After highlighting the node to be replaced in the rule builder window, the user selects the replace option 142 on the toolbar. Upon selecting the replace option, the user is provided with another list in the form of a drop down menu of available nodes for insertion in the rule builder window. By selecting a node from the provided drop down menu, the highlighted node in the rule builder window is replaced with the selected node. In the example provided, the user has highlighted the hold node 150 in FIG. 3, and the hold node is shown in the rule builder window 126 highlighted with a bold outline. In FIG. 4, the user has selected a range node 152 from the drop down menu associated with the replace option 142, and the hold node 150 (previously shown in FIG. 3) has been replaced by the range node 152.

As described above, when a node is selected from the insert menu 141 or the replace menu 142, the node appears in the rule builder window 126. Certain nodes selected for insertion in the rule builder window will require configuration. When a selected node requires configuration, a configuration box appears in the rule builder window which prompts the user to insert all necessary data required to properly configure the node. For example, as shown in FIG. 4, when the user selects the range node 152, a configuration box 170 appears in the rule builder window 126. The configuration box 170 instructs the user to enter the proper data in order to configure the node. In the example of FIG. 4, the user must configure the range node 152 by specifying a current or past test result and specifying a particular range for comparison.

In some instances, nodes may be configured in different manners. For example, a range node, such as the one shown in FIG. 4, may be configured based on numerical limits inserted by the user or based on named ranges which are predefined by the laboratory for the particular test. Thus, in some instances the user may insert a numbers in the configuration box to define the lower limit and upper limit for the node. In other instances, the user may select one of several named ranges, each named range having a predefined upper limit and a predefined lower limit. Examples of named ranges include a validation range, a reference range, or a critical range.

When a range node is designed in this manner such that the user is not required to insert specific details (such as numerical values) for the range, it is considered a common node. A common node one in which the node's configuration is independent of the specific test in which the node is used. If specific details are required in association with the configuration of the node for a particular rule, those details are predetermined by the laboratory and are automatically retrieved when the common node is inserted into the rule. Thus, common nodes allow the user to easily build autoverification rules without having to pull specific details related to the test result being analyzed, such as specific acceptable ranges for different test results.

FIG. 4 shows an embodiment where the range node 152 is configured as a common node. In this embodiment of the range node 152, the user configures the node by simply selecting one of several named ranges. The numerical values associated with the named range have already been predefined by the laboratory for the particular test in which they are used. In FIG. 4, the user has selected the "validation range" from the lower drop down menu 172 of the configuration box 170. The validation range is a predefined range determined by the laboratory where test results falling within the range will be considered valid test results for the particular test results being analyzed by the rule. For the serum calcium autoverification rule of FIG. 4, the laboratory may predefine the validation range to be between 2 and 20 mg/dL. This means that the lab considers any test result within this range to be consistent with what can be considered a realistic test result from a serum calcium test. However, if the laboratory receives a result of 50 mg/dL, the system will consider this to be an unrealistic test result for serum calcium, and the lab will assume that some error has been made in the analysis.

Similar to the "validation range", the laboratory may define other ranges, such as a "reference range" or a "critical range" for the range node 152 when used as a common node. For example, the laboratory may define the reference range for serum calcium to be between 9 and 10.5 mg/dL. This means that a serum calcium test result within this range is considered normal, and the test result does not indicate an issue for the patient. As another example, the laboratory may define the critical range for serum calcium to be between 8 and 15 mg/dL. This means that a serum calcium test result outside of the critical range suggests a critical issue for the patient. In this case, the system may be configured to immediately notify the physician of the test result so that immediate attention may be given to the patient. It will be recognized that the above ranges are merely examples of ranges that may be predefined by a laboratory using the system, and numerous other ranges could be defined by the laboratory. Furthermore, while the range node 152 has been described herein as one example node that requires configuration when inserting the node into the rule builder window 126, it will be recognized that many other nodes that may be selected by the user must also be configured before they are properly included into the autoverification rule.

Once a node has been inserted into the rule builder window and configured (if required), outputs from the node must be associated with subsequent nodes. As discussed previously, all decision nodes will have at least two outputs. To assist the user with properly associating the two or more required outputs from a decision node with subsequent nodes, the editor is configured to show each of the possible outputs from a decision node when the decision node is placed in the rule builder window. Accordingly, in the example of FIG. 5, when the range node 152 is placed in the rule builder window 126 the editor immediately displays the range node 152 with three output edges 153 already extending from the node 152. The three output edges 153 extending from the node 152 advantageously remind the user that three possible outcomes may result from a range node. In particular, a range node will compare a test result to the defined range and determine whether the test result is within the defined range, above the defined range, or below the defined range. By displaying an output edge 153 for each of the three possible outcomes, the user is reminded to connect each of the three possible outcomes to a resulting node. To further assist the user, the editor extends each of the three output edges 153 from the range node 152 to a dummy node 168a-168c (i.e., an un-configured "then . . . " node).

Figure 6:
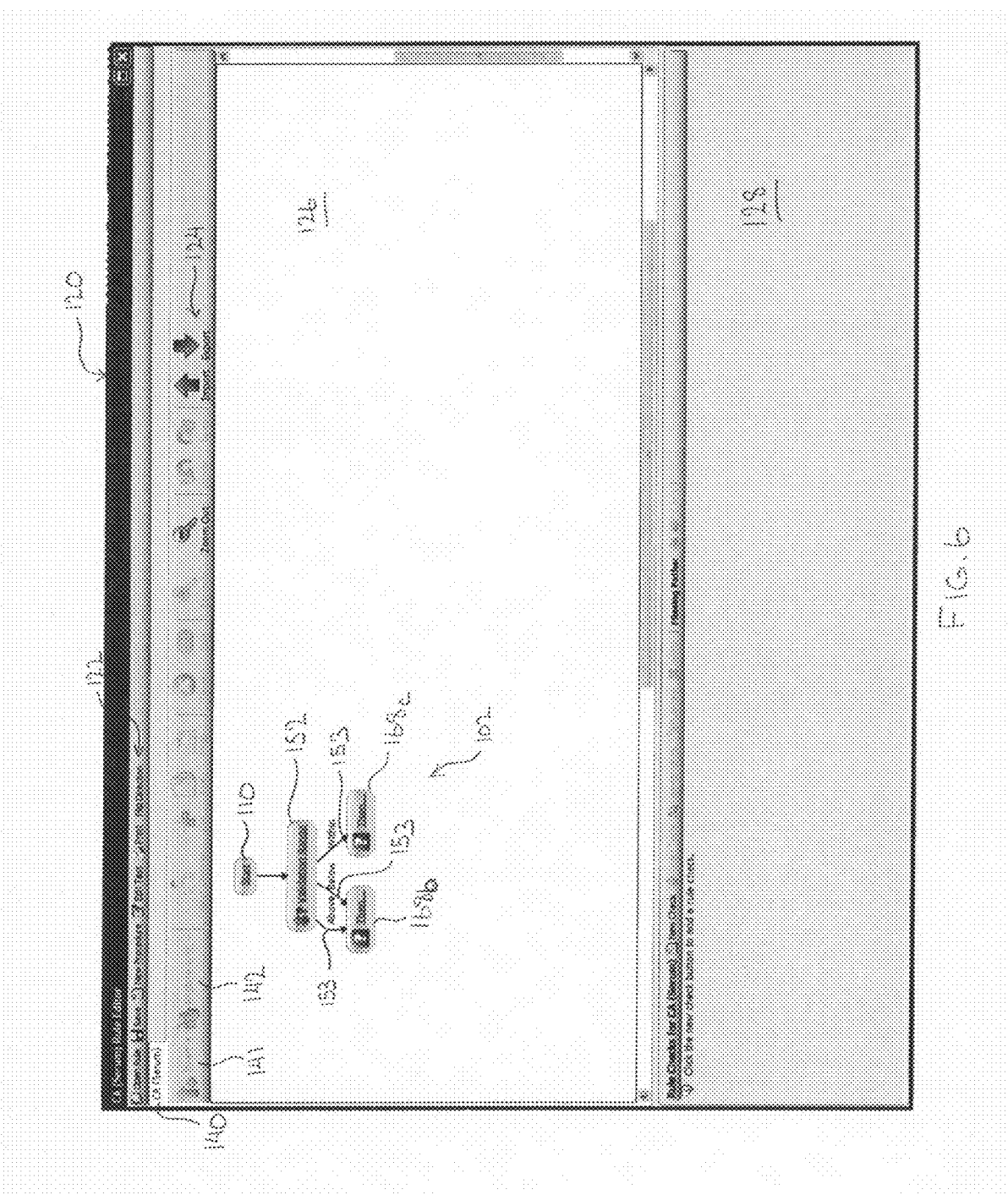
FIG. 6 shows the exemplary flowchart of FIG. 5 wherein one of the output edges of the decision node has been directed to a different node.

The output edges of a decision node which automatically appearing upon the insertion of the decision node into the rule builder window 126 may be manipulated by the user to lead to either two or three nodes. For example, in FIG. 6 the user has manipulated the output edges 153 of the range node 152 to indicate that a test result outside of the validation range leads to a first node 168b, regardless of whether the test result is above or below the validation range, and a test result within the validation range leads to a second node 168c. To accomplish this, the user simply clicks near the arrow on the "above" edge 153 shown in FIG. 5, and drags the edge to the node 168b associated with the "below" edge. The editor then automatically removes the dummy node previously associated with the "above" edge from the rule builder window 126, and both the "above" edge and the "below" edge lead to the same dummy node 168b, as shown in FIG. 6. While manipulation of edges has been described herein with respect to edges leading to dummy nodes, it will be recognized that the editor may allow manipulation of any edges within a partial or complete flowchart in a similar manner. Accordingly, the editor provides a convenient way for users to manipulate flowcharts and the node-to-node progression through the flowchart.

Figure 7:
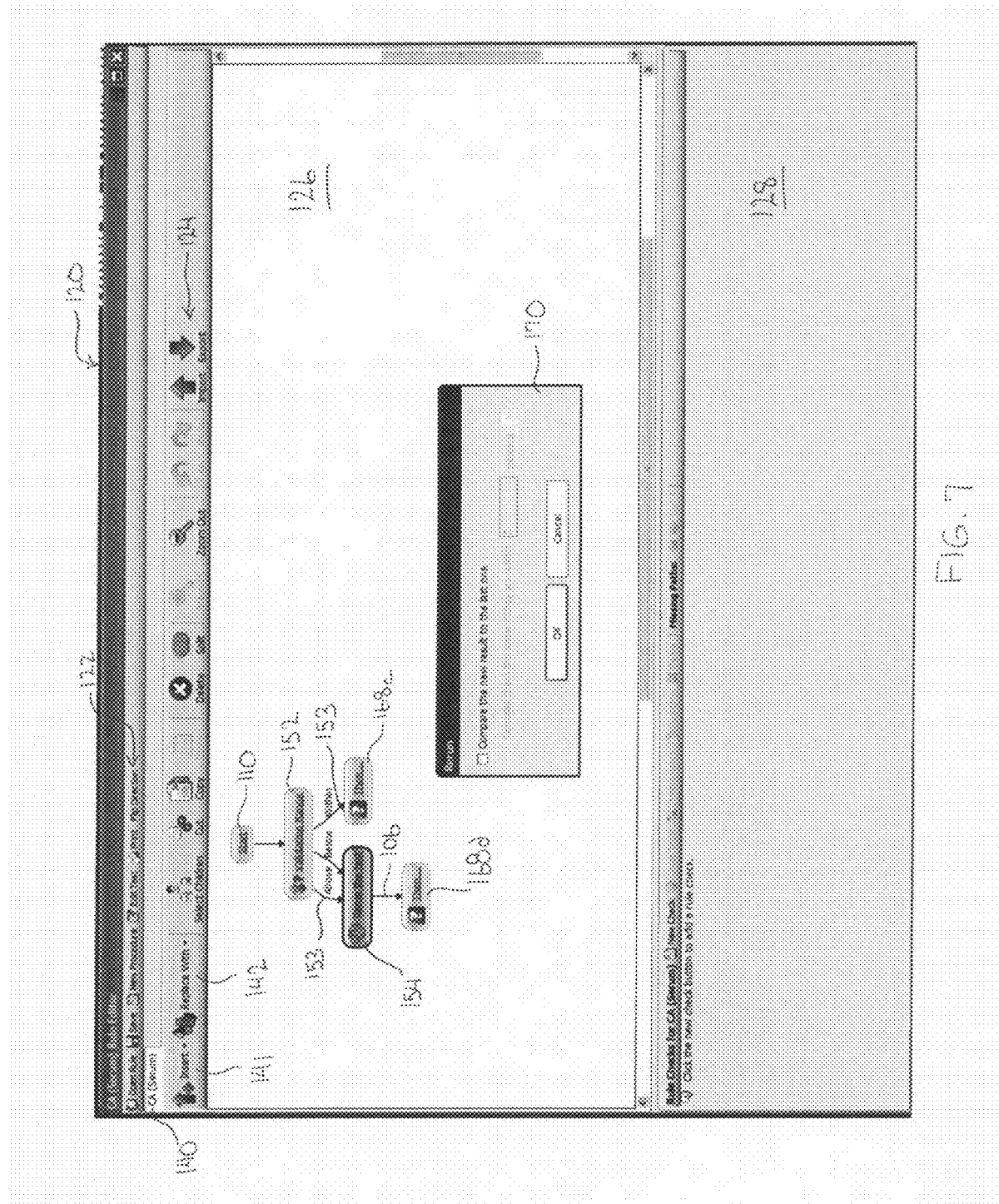
FIG. 7 shows the exemplary flowchart of FIG. 6 with a rerun node added to the flowchart and a dialog box appearing on the screen along with the flowchart.

In addition to manipulating edges within the flowchart 102, the user may also manipulate nodes by inserting new nodes or replacing existing nodes. For example, as shown in FIG. 7, the user had replaced the dummy node 168b in the rule builder window 126 with a functional node 154. This is accomplished using the replace option 142 from the toolbar 124, described above. When using the "replace" option 142, the user first highlights the node to be replaced and then selects the "replace" option 142 from the toolbar. When the "replace" option 142 is selected, the user is presented with a drop-down menu listing various nodes to replace the highlighted node. After the user selects a replacement node from the drop down menu, it automatically appears in the rule builder window 126 in place of the previously highlighted node. In the case of FIG. 7, the user has replaced the dummy node 168b following the above and below edges 153 with a "rerun" node 154.

As shown in FIG. 7, when the user selects the "rerun" node 154 for insertion, a configuration box 170 automatically appears in the rule builder window 126, instructing the user to properly configure the "rerun" node 154. At the same time, a new dummy node 168d is provided in the rule builder window 126 on the output edge 106 of the "rerun" node.

Figure 8:
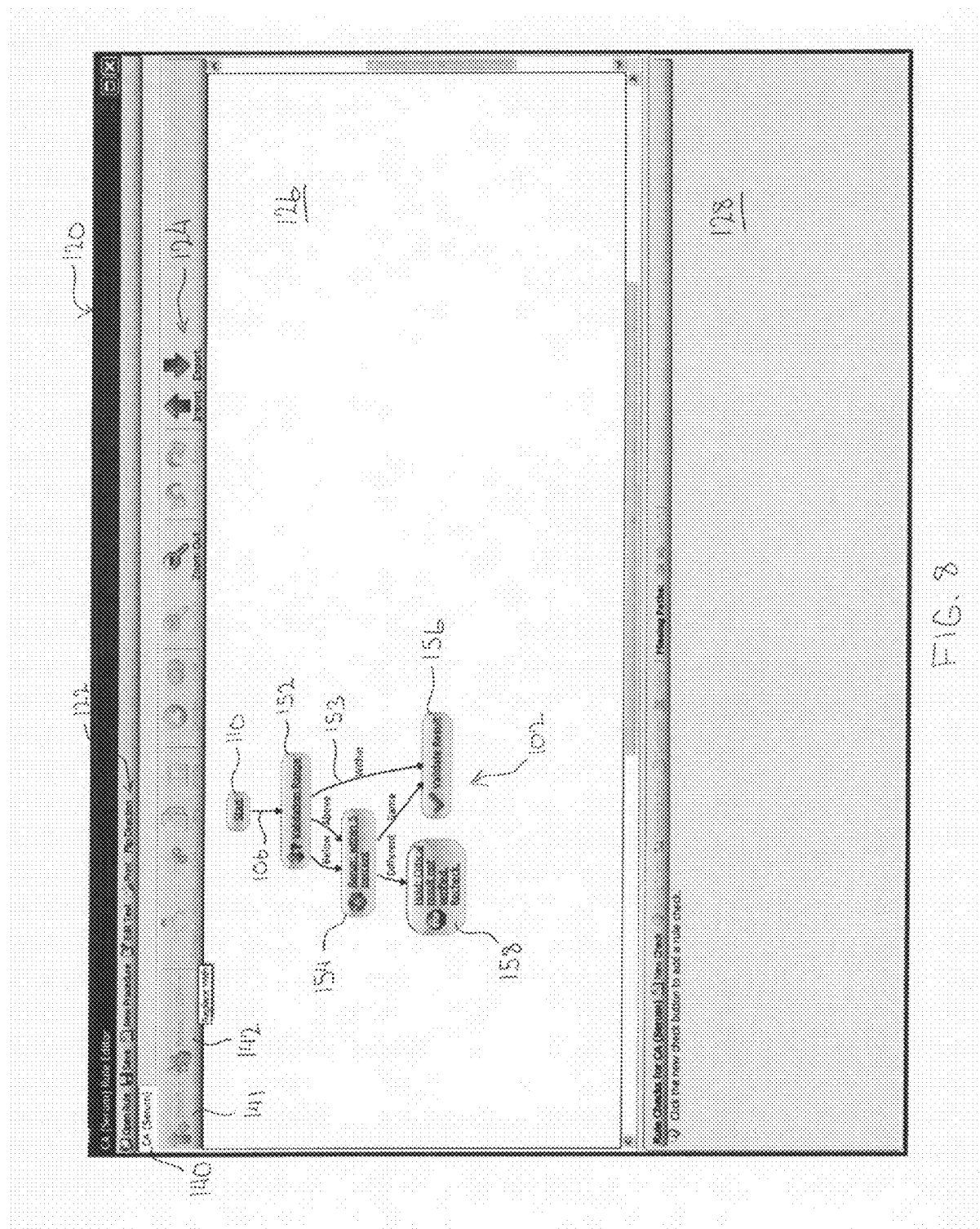
FIG. 8 shows the exemplary flowchart of FIG. 7 including further nodes and redirected edges.

FIG. 8 shows that the "rerun" node 154 has been configured by the user. As a result of the configuration, the "rerun" node now includes two output edges, and the node has instructions to compare the rerun test result to the previous test result. Thus, the "rerun" node 154 is an action node that is also configured to make a decision related to the action. In the embodiment of FIG. 8, the user has configured the "rerun" node 154 to rerun the original test result since it fell outside of the validation range. The node 154 has also been configured to compare the new test result following the rerun to the previous test result. As also shown in FIG. 8, if the rerun test result is not within five percent of the previous test result, the rule holds the test result at hold node 158, which indicates that the test result is an invalid test result outside of the validation range and should be manually checked by the user. However, if the rerun test result is within five percent of the previous test result, the rule has been configured to validate the test result at the validate node 156.

As also shown in FIG. 8, the user has clicked the "within" output edge 153 from the range node 152 and dragged it down to the validate node 156. Upon validation, test results are noted as validated within the information system (e.g., the LIS) and may be released for observation in other information systems (e.g., the HIS).

As discussed above with reference to FIGS. 3-8, the editor allows the user to build an autoverification rule as a flowchart shown on a graphical user interface. The user may easily insert new nodes as well as replace existing nodes in order to build the desired rule. In addition, the user may easily manipulate edges extending between nodes and define the node-to-node progression through the flowchart. The editor's flowchart-based language is generally intuitive and facilitates the user's expression of a desired autoverification procedure.

Creation and edition of autovalidation rules have been described above with respect to the "insert" option 141 and "replace" option 142. However, it will be recognized that numerous other options may be provided in the menu 122 or toolbar 124 for building and editing autoverification rules. For example, the select children option 143, which was not discussed above allows the user to specify subsequent nodes or "children" following an action node that does not automatically create edges and connected dummy nodes when placed in the rule builder window. Another example of a tool that may be provided for the user is the ability to define node macros. Macros include a plurality of nodes connected in a certain order but not specifically associated with a particular autoverification rule. These macros may then be selected from a menu and inserted into different autoverification rules. In one embodiment, the macros are not configurable and can not be specialized for a particular rule. However, in another embodiment, some macros may be designed such that configuration and specialization for particular rule is possible.

Once an autoverification rule is created, it is saved by the system in data storage 20 (see FIG. 1) and is available for execution by the processor 16 when a test order associated with the autoverification rule is received in the laboratory. A test order typically includes at least one test to be run by a laboratory analyzer and data related to the patient associated with the test order (e.g., name, age, sex, weight, height, etc.). Test orders may be received automatically via a computer network, or may be manually entered into the system by a laboratory technician. When a test order is received by the laboratory it is accompanied by a test sample. The test sample is delivered to the appropriate laboratory analyzer (or manual analyzer station) so the designated test can be performed on the sample.

Execution of an autoverification rule associated with a test order begins when the system receives the test order. Upon receipt of the test order, the system pulls the saved autoverification rule from memory or data storage and proceeds with execution of the rule.

Execution of each rule begins with the start node. Thereafter, the rule proceeds from node-to-node 104 as directed by the edges 106. When reaching a new node, the system calls the routines associated with the node including any logic and side-effects. Upon performing the routines associated with the node 104, the defined rule indicates whether the system should stop rule execution, wait for a new result, or follow one of the output edges 106 from the node to a new node 104 and begin execution of the new node. When the rule reaches an action node with no output edges, the rule terminates. The rule does not execute again until a new test order calling for the rule is received. If desired, the user may display the flowchart representation 102 of the autoverification rule on the graphical user interface 14 during execution. However, in most instances, the processor will execute the rule without displaying it on the graphical user interface.

The laboratory will typically receive multiple test orders for multiple samples at one time. Accordingly, the processor 16 may run multiple autoverification rules in parallel. This may include simultaneously running two or more instances of the same autoverification rule on two or more different test orders and/or simultaneously running two or more different autoverification rules on two or more different test orders.

As mentioned above, during the execution process an autoverification rule may be suspended and instructed to wait. A typical example of a situation where a rule suspends is where a node can not be executed because necessary data is unavailable. For example, if the rule of FIG. 8 is executed, the rule must wait at node 152 to receive a serum calcium test result from the laboratory analyzer before moving on to subsequent nodes 154 or 156. Thus, when a test order for serum calcium is received, the rule suspends at node 152 until the laboratory analyzer produces the serum calcium test result. In this situation, a rule will suspend indefinitely until it receives the serum calcium test result or is cancelled by the user. If a rule is terminated by the user, the system generates an error notice. The test result is then passed on to the laboratory technician for handling. The technician can then manually determine whether the test result is valid.

FIG. 8 also provides another example of a situation where a rule may suspend. Upon reaching the rerun node 154, the previously executed test is re-ordered by the system, and the rule is suspended until the new test result is received. In order to accomplish this, the system may issue a notification to the laboratory technician to place the sample tube back on the laboratory analyzer. Alternatively, if the system includes robotics or some other mechanized sample transportation device, the system may automatically rerun the test through the laboratory analyzer and the laboratory technician would not be notified at all. In this situation, the rerun is handled entirely by the system.

Figure 9:
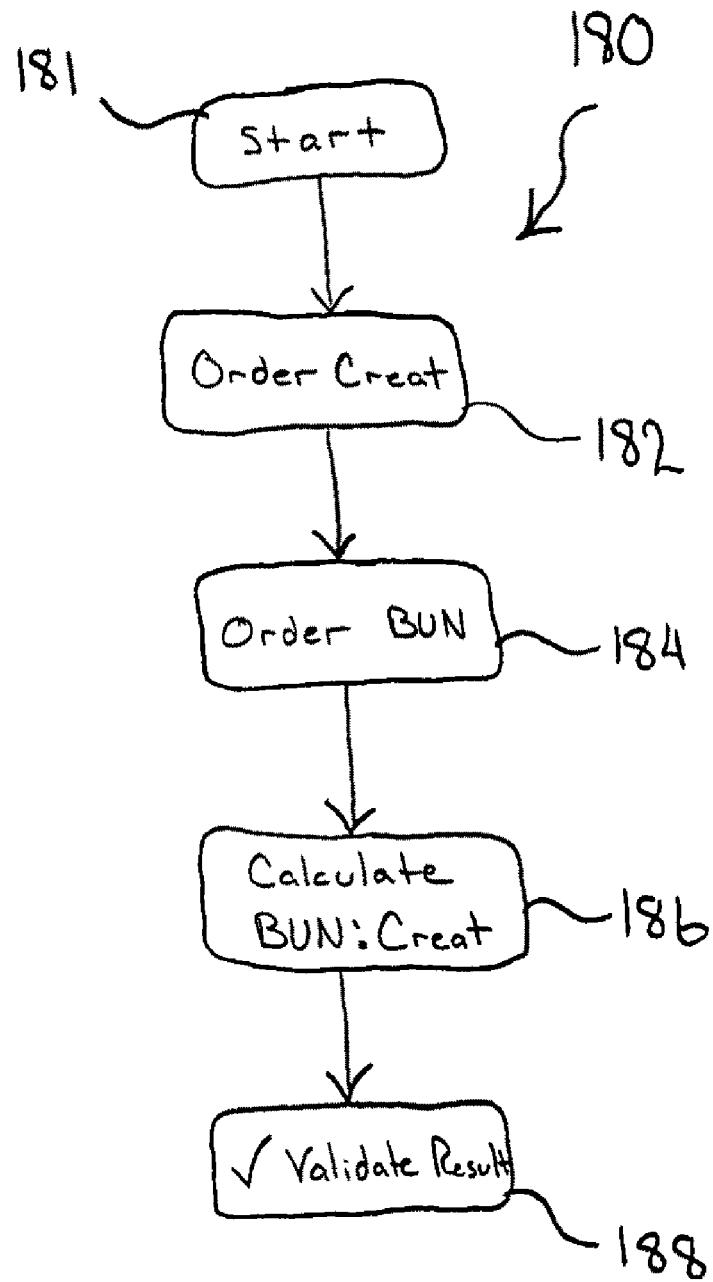
FIG. 9 shows yet another exemplary flowchart for use with the autoverification system of FIG. 1.

It will be recognized that a rerun on a test sample could also occur for numerous other reasons without a rule specifically asking for a rerun. For example, a technician may realize that an analyzer has not been properly calibrated, and may rerun all tests recently performed using the analyzer. In these situations, an autoverification rule that depends on the rerun test result in a particular node does not restart or otherwise take any special action when the rerun test result is received. However, the autoverification rule that depends upon the rerun test result in a particular node will utilize the rerun test result rather than the previous test result. Thus, the autoverification rule in this case is does not return to the start node, but is instead restarted from the node that depends on the actual rerun test result. As an example of this, consider FIG. 9 which shows a simple BUN-creat autoverification rule 180. According to this rule, a creatinine ("creat") test is ordered at node 182 and then a BUN test is ordered at node 184. Based on the results of these two tests, a ration of BUN to creat is calculated at node 186, and the test is then validated at node 188. If a rerun of the creat test occurs for some reason, the autoverification rule of FIG. 9 does not need to begin at the start node 181. Instead, the autoverification rule restarts at the calculation node 186 simply incorporating the rerun test result for creat and the existing test result for BUN to arrive at the specified calculation. Thus, the rule avoids another creat order and another BUN order which would otherwise be associated with nodes 182 and 184 if the entire rule were run from the start node. Instead, the rule is simply restarted at node 186 using the available data.

Although the present invention has been described with respect to certain preferred embodiments, it will be appreciated by those of skill in the art that other implementations and adaptations are possible. Moreover, there are advantages to individual advancements described herein that may be obtained without incorporating other aspects described above. Therefore, the spirit and scope of the appended claims should not be limited to the description of the exemplary embodiments contained herein.

What is claimed is:

1. A method for creating an autoverification rule for generating and validating laboratory test results from a first analysis performable by a laboratory analyzer on patient samples, the method comprising:
   presenting to a user a graphical user interface of a computer from which the user may select nodes and construct a flow chart representing the autoverification rule, the nodes including at least one of:
     an order test node that directs a laboratory analyzer to perform a test on the patient sample;
     a rerun node that directs the laboratory analyzer to automatically rerun the first analysis on the patient sample;
     a range check node that determines if a value of the laboratory test results is inside, below, or above a validation range provided by the user based on the first analysis and the laboratory analyzer; and
     a delta check node that retrieves prior laboratory test results generated by the first analysis and compares the laboratory test results and the retrieved prior laboratory test results;
   receiving a plurality of user instructions for creating the flow chart including user selections of nodes and user entry of criteria for at least one node to be applied to the laboratory test results generated by the first analysis of patient samples by the laboratory analyzer;
   generating a flow chart representing the autoverification rule specific to the first analysis performed by the laboratory analyzer based on the user selections;
   displaying the flow chart representing the autoverification rule specific to the first analysis to the user; and
   generating the autoverification rule corresponding to the displayed flow chart, wherein the autoverification rule is specific to the first analysis performed by the laboratory analyzer that generates the laboratory test results and is usable by an autoverification system to determine if the laboratory test results generated by the first analysis of the patient sample by the laboratory analyzer should be automatically released to an external information system.

2. The method of claim 1 further comprising:
   storing the autoverification rule corresponding to the displayed flow chart;
   automatically upon receipt of a test order to analyze a sample by the first analysis,
     retrieving the autoverification rule corresponding to the displayed flow chart; and
     executing the autoverification rule corresponding to the displayed flow chart to control, at least in part, the operation of the laboratory analyzer.

3. The method of claim 2 wherein the presented nodes further comprise a set value node that replaces a value in the test results with a predetermined value.

4. The method of claim 1 further comprising:
   upon execution of the order test node, transmitting a command directing the laboratory analyzer to perform the first analysis on the sample; and
   suspending execution of the autoverification rule until test results are received.

5. The method of claim 1 further comprising:
   upon execution of the rerun node, transmitting a command directing the laboratory analyzer to automatically rerun the first analysis on the sample; and
   suspending execution of the autoverification rule until new test results are received.

6. The method of claim 1 further comprising:
   upon execution of the delta check node, retrieving prior test results generated by the first analysis on a prior sample associated with the patient; and
   comparing current test results and the retrieved prior test results.

7. The method of claim 1 wherein the receiving operation includes receiving a user selection of at least two nodes including a validate node and the method further comprises:
   storing the autoverification rule corresponding to the displayed flow chart;
   automatically upon receipt of a test order to analyze a sample by the first analysis,
     retrieving the autoverification rule corresponding to the displayed flow chart; and
     executing the autoverification rule corresponding to the displayed flow chart to validate new test results stored on a laboratory information system, the new test results generated by performance of the first analysis on the sample; and
   upon execution of the validate node, releasing the new test results.

8. The method of claim 7 wherein the releasing operation comprises:
   providing access to the new test results to a hospital information system external to the laboratory information system.

9. The method of claim 8 wherein the releasing operation further comprises:
   automatically transmitting the new test results to the hospital information system.

10. The method of claim 1, wherein receiving the plurality of user instructions comprises:
    receiving a selection of an option associated with a given node; and
    receiving data in a configuration box, the configuration box displayed in the graphical user interface, the configuration box prompting the user to insert data required to configure the given node.

11. A system for generating and autoverifying an electronic laboratory test result of an analysis of a sample, the system comprising:
    a laboratory analyzer that performs a first analysis on the sample and generates the electronic laboratory test result;
    an autoverification rule editor that presents a user interface through which a user may create autoverification rule flow charts specific to analyses performed by the laboratory analyzer based on user selections and that generates autoverification rules corresponding the created flow charts, each of the flow charts represented by a plurality of connected nodes, the plurality of connected nodes including one or more of:
an order test node that directs a laboratory analyzer to perform a user-selected analysis on the patient sample;
a rerun node that directs the laboratory analyzer to automatically rerun the first analysis on the patient sample; and
a range check node that determines if a value of the laboratory test result is inside, below, or above a validation range provided by the user based on the first analysis and the laboratory analyzer; and
a delta check node that retrieves a prior laboratory test result generated by the first analysis and compares the laboratory test result and the retrieved prior test result;
one or more autoverification rules generated by the autoverification rule editor from flow charts created by a user including a first autoverification rule specific to the first analysis performed by the laboratory analyzer corresponding to a flow chart specific to the first analysis; and
a processor having access to the electronic laboratory test result and the first autoverification rule that releases the electronic laboratory test result to an information system based on the first autoverification rule specific to the first analysis performed by the laboratory analyzer.

12. The system of claim 11 wherein the processor further automatically identifies and executes the first autoverification rule upon receipt of a test order requesting performance of the first analysis on a sample.

13. The system of claim 12 wherein the computer commands the laboratory analyzer to perform at least one of the following: automatically perform the first analysis on the sample in response to an order test node in the flow chart; automatically rerun the first analysis on the sample in response to a rerun node in the flow chart; automatically cancel a previously ordered first analysis on the sample in response to an cancel test node in the flow chart; automatically dilute and rerun the first analysis on the sample in response to a dilute node in the flow chart; automatically determine if a value of the electronic laboratory test result is inside, below, or above a validation range provided by the user based on the first analysis and the laboratory analyzer in response to a range node in the flow chart, and automatically releases the electronic laboratory test result to an information system in response to a validate node.

14. The system of claim 11 wherein the plurality of connected nodes includes:
a validate node that directs the processor to automatically release the laboratory test result to the information system and that stores an indication that the test result is validated.

15. The system of claim 11 wherein the plurality of connected nodes includes:
a dilution node that causes the processor to automatically command the laboratory analyzer to dilute the sample by a user-selected amount and rerun the first analysis on the sample.

16. The system of claim 11 wherein the plurality of connected nodes includes:
a cancel test node that causes the processor to cancel performance of a user-selected analysis by the laboratory analyzer on the sample.

17. The system of claim 11 wherein the plurality of connected nodes includes:
a manual workflow node that causes the processor to request an action to be performed by a laboratory technician.

18. The system of claim 11 wherein the plurality of connected nodes further includes a set value node that replaces a value in the laboratory test results with a predetermined value.

19. The system of claim 11 wherein the computer controls the operation of the laboratory analyzer based on the flow chart specific to the first analysis generated by the autoverification rule editor from user inputs.

20. The system of claim 11, wherein the autoverification rule editor displays options associated with the plurality of nodes, receives a selection of a given one of the options, the given one of the options associated with a given node in the plurality of nodes, the autoverification rule editor inserting the given node into a given one of the flow charts, displaying output edges for each outcome of the given node, and reminding the user to connect each of the outcomes to a resulting node.

21. A method for creating a computer-executable autoverification rule for verifying laboratory test results generated by a first analysis performable by a laboratory analyzer on patient samples, the method comprising:
receiving a first user definition of a reference range for a plurality of laboratory analyses including a first analysis, the first user definition identifying a first name and an independently selected range for each of the plurality of laboratory analyses including a first range associated with the first analysis;
presenting to a user a graphical user interface from which the user may select nodes and construct, by connecting selected nodes, a flow chart representing steps of an autoverification rule, wherein the presented nodes include at least one common node through which the user may select the first name of the reference range;
receiving a plurality of user instructions for creating a flow chart for the first analysis including an identification of the first analysis and, as part of a user's selection of a common node during construction of the flow chart for the first analysis, a user selection of the first name of the reference range;
generating the flow chart specific to the first analysis performed by the laboratory analyzer based on the user selections;
displaying the flow chart specific to the first analysis to the user via the graphical user interface; and
generating an autoverification rule executable by a computer, the autoverification rule corresponding to the displayed flow chart, wherein the autoverification rule is specific to the first analysis performed by the laboratory analyzer that generates the test results and the autoverification rule includes a comparison of the test results with the first range associated with the first analysis for the reference range having the first name.

22. The method of claim 21 further comprising:
retrieving the first range associated with the first analysis for the reference range corresponding to the first name from memory.

23. The method of claim 21 wherein receiving the first user definition further comprises:
receiving a plurality of user definitions of reference ranges for a plurality of laboratory analyses including the first user definition, wherein each user definition identifies a name and an independently selected range for each of the plurality of laboratory analyses; and storing the plurality of user definitions in memory.

24. The method of claim 21 further comprising:

storing the autoverification rule corresponding to the displayed flow chart;

automatically upon receipt of a test order to analyze a sample by the first analysis, retrieving the autoverification rule corresponding to the displayed flow chart; and executing the autoverification rule corresponding to the displayed flow chart to control, at least in part, the operation of the laboratory analyzer.

* * * * *